(12) United States Patent
Welles et al.

(10) Patent No.: US 11,436,935 B2
(45) Date of Patent: Sep. 6, 2022

(54) SYSTEM, METHOD AND APPARATUS FOR DRIVER TRAINING SYSTEM WITH STRESS MANAGEMENT

(71) Applicant: Advanced Training System LLC, St. Petersburg, FL (US)

(72) Inventors: Reginald T. Welles, Salt Lake City, UT (US); Darrell R. Turpin, Alpine, UT (US); Aaron J. Turpin, Taylorsville, UT (US)

(73) Assignee: Advanced Training Systems, Inc, St. Petersburg, FL (US)

( * ) Notice: Subject to any disclaimer, the term of this patent is extended or adjusted under 35 U.S.C. 154(b) by 208 days.

(21) Appl. No.: 16/535,365

(22) Filed: Aug. 8, 2019

(65) Prior Publication Data

US 2020/0005663 A1  Jan. 2, 2020

Related U.S. Application Data

(63) Continuation-in-part of application No. 15/481,819, filed on Apr. 7, 2017, now abandoned, which is a continuation-in-part of application No. 13/944,563, filed on Jul. 17, 2013, now Pat. No. 9,646,509, which is a continuation-in-part of application No. 12/889,448, filed on Sep. 24, 2010, now Pat. No. 8,770,980.

(60) Provisional application No. 61/277,768, filed on Sep. 29, 2009.

(51) Int. Cl.
*G09B 9/052* (2006.01)
*A61B 5/18* (2006.01)
*G09B 19/16* (2006.01)
*G06V 20/59* (2022.01)

(52) U.S. Cl.
CPC ............... *G09B 9/052* (2013.01); *A61B 5/18* (2013.01); *G06V 20/597* (2022.01); *G09B 19/167* (2013.01)

(58) Field of Classification Search
CPC .. G09B 9/04; G09B 9/052; A61B 5/16; A61B 5/18
See application file for complete search history.

(56) References Cited

U.S. PATENT DOCUMENTS

| | | |
|---|---|---|
| 3,309,794 A | 3/1967 | Greenshields |
| 3,479,750 A | 11/1969 | Swanson |
| 3,583,079 A | 6/1971 | Koci |
| 3,611,589 A | 10/1971 | Wiltse |
| 3,896,564 A | 7/1975 | Dewey et al. |

(Continued)

*Primary Examiner* — Peter R Egloff
(74) *Attorney, Agent, or Firm* — Larson & Larson, P.A.; Frank Liebenow; Justin P. Miller

(57) ABSTRACT

A method of training a trainee includes a sensor configured to measure at least one biological indicator of stress in the trainee. The method includes presenting a training segment in the simulation while monitoring inputs from the trainee. Data is read from the sensor and an instantaneous stress level of the trainee is calculated from the data. If the instantaneous stress level greater than a predetermined value, a stress-change feature is selected that will reduce stress and applying the stress-change feature to the training segment, thereby reducing complexity of the training segment for reducing the instantaneous stress of the trainee. for example, the stress-change feature is changing the weather, adding/removing bad drivers, adding/removing pedestrians, etc.

20 Claims, 9 Drawing Sheets

(56) References Cited

U.S. PATENT DOCUMENTS

| | | |
|---|---|---|
| 3,936,955 A | 2/1976 | Gruen |
| 4,034,484 A | 7/1977 | Radice |
| 4,464,117 A | 8/1984 | Foerst |
| 4,683,891 A | 8/1987 | Cornellier et al. |
| 5,116,051 A | 5/1992 | Moncrief et al. |
| 5,197,003 A | 3/1993 | Moncrief et al. |
| 5,277,584 A | 1/1994 | DeGroat et al. |
| 5,366,376 A | 11/1994 | Copperman |
| 5,377,100 A | 12/1994 | Pope et al. |
| 5,399,091 A | 3/1995 | Mitsumoto |
| 5,626,362 A | 5/1997 | Mottola |
| 5,707,237 A | 1/1998 | Takemoto |
| 5,823,876 A | 10/1998 | Unbehand |
| 5,921,780 A | 7/1999 | Myers |
| 5,951,018 A | 9/1999 | Mamitsu |
| 5,993,216 A | 11/1999 | Stogner |
| 6,012,926 A | 1/2000 | Hodges et al. |
| 6,105,737 A | 8/2000 | Weigert |
| 6,227,862 B1 | 5/2001 | Harkness |
| 6,270,350 B1 | 8/2001 | Christopher |
| 6,431,872 B1 | 8/2002 | Shiraishi |
| 6,450,820 B1 | 9/2002 | Palsson et al. |
| 6,623,428 B2 | 9/2003 | Miller et al. |
| 6,916,074 B2 | 7/2005 | Jung |
| 6,994,361 B2 | 2/2006 | Nishimura |
| D531,221 S | 10/2006 | Shiraishi |
| 7,625,287 B2 | 12/2009 | Champagne |
| 8,439,686 B2 | 5/2013 | Zayfert et al. |
| 2003/0097047 A1 | 5/2003 | Woltermann et al. |
| 2004/0158476 A1 | 8/2004 | Blessinger |
| 2004/0259059 A1 | 12/2004 | Aoki |
| 2005/0090757 A1 | 4/2005 | Kuramori et al. |
| 2006/0040239 A1 | 2/2006 | Cummins |
| 2008/0064014 A1 | 3/2008 | Wojtczak |
| 2008/0082372 A1 | 4/2008 | Burch |
| 2009/0098519 A1 | 4/2009 | Byerly |
| 2009/0163283 A1 | 6/2009 | Childress |
| 2009/0306880 A1 | 12/2009 | Gomi |
| 2010/0010371 A1 | 1/2010 | Zayfert |
| 2011/0009193 A1 | 1/2011 | Bond et al. |
| 2011/0260873 A1 | 10/2011 | Ouchi |
| 2013/0250080 A1* | 9/2013 | Farrell ............... G08B 21/0283 348/77 |
| 2013/0316313 A1 | 11/2013 | Darrow |
| 2017/0162072 A1* | 6/2017 | Horseman ................ G09B 7/02 |

* cited by examiner

SYSTEM, METHOD AND APPARATUS FOR DRIVER TRAINING SYSTEM WITH STRESS MANAGEMENT

CROSS-REFERENCE TO RELATED APPLICATION

This application is a continuation-in-part of U.S. patent application Ser. No. 15/481,819, filed Apr. 7, 2017 which in turn is a continuation-in-part of U.S. patent application Ser. No. 13/944,563, filed Jul. 17, 2013 and issued as U.S. Pat. No. 8,770,980 on Jul. 8, 2014, the disclosure of which is hereby incorporated by reference. U.S. patent application Ser. No. 13/944,563 claims the benefit of U.S. provisional application No. 61/277,768 filed on Sep. 29, 2009, the disclosure of which are incorporated by reference.

FIELD

This invention relates to the field of training and more particularly to a training system with stress management.

BACKGROUND

Driving training simulators are well known. Such simulators often included controls that simulate the target vehicle (e.g. car, truck, bus, etc). It is known that such simulators improve skills and safety by familiarizing the trainee with operation of the vehicle by presenting simulated situations in which, making the wrong decision does not result in a potential accident that may cause bodily harm. In this way, the trainee learns basic driving skills before they eventually need to perform using the actual target vehicle and before they have to perform using that vehicle while operating in traffic, but in a simulated way that imposes a real feeling of driving, and therefore, fear of getting hurt or hurting someone else.

There are many types of simulators known. The simplest simulator is a typical driving video game having a display screen and a hand controller. In some systems, a simulated steering wheel is provided. A mock-vehicle is displayed on the display screen and the driver uses the hand controller to keep the mock-vehicle on a simulated, moving roadway on the display screen. This type of simulator helps build hand and eye coordination, but does not provide the true control operation of the real steering wheel, brake, clutch, shifter, windshield views and mirror views. These types of simulators are more of a game than an actual driver training system.

Another type of simulator includes a video display screen to simulate a windshield view, a steering wheel, a gas pedal, a brake pedal, a shifter and, optionally, a clutch pedal. A road situation is displayed on the display screen and the driver uses the controls to drive the simulated vehicle, moving down a roadway that is displayed on the display screen. This type of simulator helps build driver skills, but does not include interaction with speedometers, tachometers, etc. Such simulators don't provide feedback from the shifter such as gear grinding when the clutch isn't operated correctly. Furthermore, such simulators have a fixed configuration relating to a single type/layout of vehicle. In some such simulators, certain gauges are provided to simulate the operation and information provided to a driver of this simulated vehicle. Present-day simulators provide fixed scenarios to the trainee and evaluate the trainee responses in a fixed program, progressing from scenario to scenario in a linear progress.

As the realism of such simulations increases, for example, utilizing realistic rear-view mirrors as described in U.S. Pat. No. 9,418,568 issued Aug. 16, 2016, which is included by reference, the potential for "simulator associated sickness." Simulator associated sickness also occurs when the simulator impacts a different feeling to the trainee with respect to what the trainee is seeing (e.g. the trainee turns the vehicle to the right, but feels like the vehicle moves to the left). Such feelings are possible, especially in complicated systems in which the simulator platform includes a motion component such as described in U.S. Pat. No. 9,852,650 issued Dec. 26, 2017, which is also included by reference. Simulator associated stress is somewhat similar to sea sickness, and if you have been around a person with sea sickness, you understand why any hope of further learning ceases once simulator associated sickness occurs.

Driving a large truck on today's crowded highway demands that a driver have complex psychomotor skills, visuospatial coordination, vigilance and good judgement. The actual environment in which the driver operates such a truck does not lend itself to a training situation where a person trains another in the driving task (like driver's education).

Adequate training for highway driving of a commercial vehicle must include training for a number of unexpected events that often occur during the career of the truck driver while operating their vehicle. The most effective and safest way to train the driver/trainee as to how to respond to these events is through the use a high-fidelity simulator.

The Federal Aviation Administration (FAA) has for many years mandated simulator training on a recurring basis for all commercial aircraft pilots in the United States. The same simulation training requirement has not been mandated for commercial truck drivers, mainly due to the sheer number of drivers and the lack of affordable simulators. However, recent advances in simulator technology and costs, along with industry interest, have increased the use of heavy truck simulators in both training schools and trucking company's fleets. As with aviation simulator training, the most effective use of truck simulators is with the simulation of unexpected situations where the operator must react in seconds to avoid a catastrophic outcome. Unlike aircraft simulators, truck simulators typically operate without a full-time instructor assigned to each driver being trained. Also, for financial reasons, the truck simulators need to operate on a 24/7 basis with minimum instructor input.

Psychologists who are experts in the process of learning indicate that there is a strong relationship between stress and learning, and this relationship is more complex than most people would assume. Mild to moderate levels of stress improve memory of the tasks performed, and therefore learning. On the other hand, high levels of stress have been shown to be harmful to memory and memory-related performance and learning. Likewise, very low levels of stress lead to boredom and, hence, little learning.

Stress is also very much an individualist event. Two people with elevated levels of stress often respond quite differently to learning. Because of this individual difference, each trainee needs to be continually measured for stress to determine when the stress impacts performance, but no existing training system does this.

An example of this is simple school learning. A child who is bored in the classroom is often distracted, daydreaming, not paying attention; and therefore, not learning. A child, who is overloaded, taking too many courses, unable to see a light at the end of the semester, becomes over stressed and, even if able to achieve passing grades, will likely not retain what they have learned.

Often, as the simulation difficulty exceeds the trainee's abilities, stress is experienced by the trainee. For example, when the simulation becomes overwhelming because too many problems are occurring such as severe simulated weather coupled with bad drivers and dangerous roads, often the trainee will experience excess stress. Some stress is normal and expected as operating of most vehicles (cars, trucks, boats, airplanes, etc.) under realistic conditions is not always an easy task. For some trainees, too much stress will metabolize into physical and emotional problems. For example, as a trainee's stress level increases because the trainee is in a very difficult simulation, sometimes the trainee becomes ill or becomes violent. Such illness or violence has the potential to cause health problems to the trainee (e.g. a broken hand) or damage to the simulation system (abuse to the simulation system, vomiting, etc.). Short of such damage, if stress levels elevate to a certain point, it is often desired to consult with a training leader to understand the causes of the stress and to help the trainee cope with such stress because, surely, once the trainee has graduated and is operating a real vehicle, the trainee will encounter stressful situations and need to cope with such, without the help of a training leader.

Prior training systems have adjusted stress through speeding up or slowing down the simulation. This does not provide a realistic simulation, rather s surreal simulation where other vehicles and people go about like the Keystone Cops or, when slowed, like they are moving in slow motion.

What is needed is a driver training system that monitors stress of the trainee and takes steps to mitigate the stress.

SUMMARY

A training system is disclose having sensors that monitor at least one biological parameter. During training, a stress level is determined based upon data from the sensors and, if the stress level is out of bounds, the training is modified and/or personnel are notified. For example, if the stress level is too high, the complexity of the training is changed to reduce stress and/or a trainer is notified.

In one embodiment, a training system for providing training on operation of a vehicle is disclosed. The training system includes a computer that has a storage device with a plurality of training segments stored thereon and accessible by the computer. There are one or more graphics displays and a sensor that is configured to measure at least one biological indicator of stress in the trainee. Software running on the computer presents the training segments to the trainee, thereby simulating operation of the vehicle under control of the trainee by operator controls. While the software presents the training segments to the trainee, the software reads data from the sensor and the software calculates an instantaneous stress level of the trainee from the data. If the instantaneous stress level exceeds a first predetermined threshold, the software notifies a trainer. If the instantaneous stress level does not exceed the first predetermined threshold and the instantaneous stress level exceeds a second predetermined threshold, then the software selects a stress-change feature that will reduce stress and applies the stress-change feature to the training segment, thereby reducing complexity of the training segment for reducing the instantaneous stress of the trainee.

In another embodiment, a method of training a trainee in use of a vehicle is disclosed. The method uses a training system that has a computer with a storage device that has a plurality of training segments. The training system includes a sensor configured to measure at least one biological indicator of stress in the trainee. The method includes presenting one of the training segments in the simulation while (b) monitoring inputs from the trainee; the inputs are from at least a steering device and a throttle device for controlling the operation of the training system and the steering device and the throttle device are operatively coupled to the computer and are located within the training system. Data is read (c) from the sensor and (d) an instantaneous stress level of the trainee is calculated from the data. (e) If the instantaneous stress level is greater than a first predetermined value, notifying a trainer. (f) If the instantaneous stress level is not greater than the first predetermined value and is greater than a second predetermined value, a stress-change feature is selected that will reduce stress and applying the stress-change feature to the training segment, thereby reducing complexity of the training segment for reducing the instantaneous stress of the trainee. (f) Steps a-f are repeated until the simulation is finished.

In another embodiment, a computer system for training a trainee regarding the use of a vehicle is disclosed including a computer that has accessible a plurality of training segments. A plurality of controls is operatively coupled to the computer for operation by the trainee; the controls include at least a steering device, and a throttle device. A display is operatively interfaced to the computer for displaying one or more of the training segments sequentially to simulate an operation of the vehicle; the one or more training segments respond to operation of the controls by the trainee. At least one sensor is operatively coupled to the computer. The at least one sensor is configured to measure at least one biological indicator of instantaneous stress in the trainee. Software running on the computer causes the computer to present the training segments and to calculate the instantaneous stress level of the trainee from the at least one biological indicator. If the instantaneous stress level is greater than a first predetermined threshold, the software running on the computer causes the computer to notifying a trainer. If the instantaneous stress level is less than or equal to the first predetermined threshold and greater than a second predetermined threshold, the software running on the computer causes the computer to select a stress-change feature that will reduce stress and to apply the stress-change feature to the training segment, thereby a complexity of the training segment is reduced for reducing the instantaneous stress of the trainee.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1:
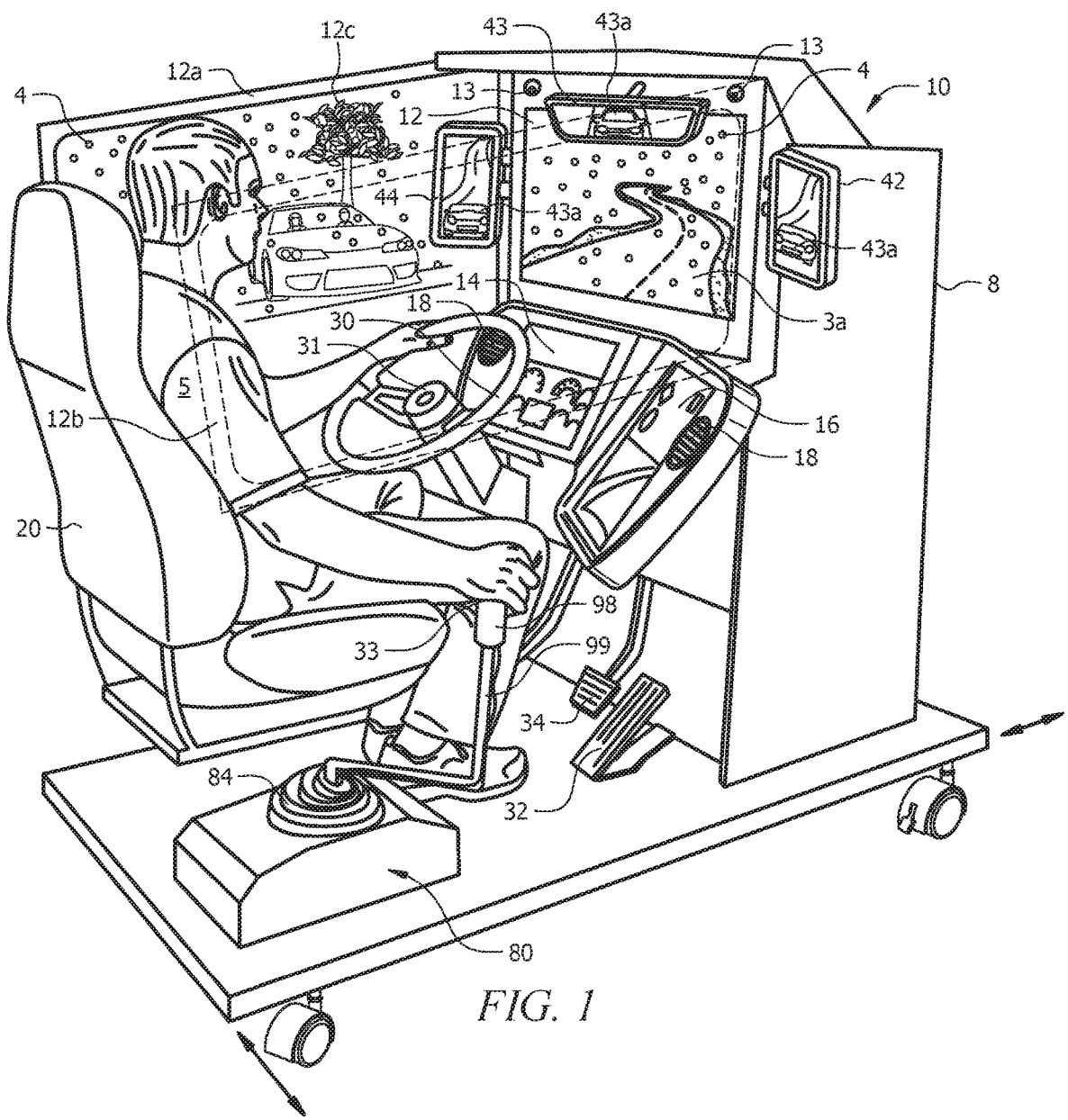
FIG. 1 illustrates a perspective view of a training system with a trainee under stress.

Reference will now be made in detail to the presently preferred embodiments of the invention, examples of which are illustrated in the accompanying drawings. Throughout the following detailed description, the same reference numerals refer to the same elements in all figures. In general, the training system 10 is often known as a driving simulator, flying simulator, boating simulator, or any other name for such a simulator, depending upon the target vehicle (car/truck, airplane, boat, train, etc). The training system 10 is any system for training a trainee (e.g. truck driver trainee) that simulates some or all of the operator controls (e.g. steering, brake, shifter) and visuals (e.g. mirrors, windows, dash boards, etc) without requiring the trainee to operate the actual vehicle (e.g., drive the actual truck). Although not limited to any particular target vehicle, the remainder of this description will use a truck as an example of such target vehicle for brevity reasons. Note that some of the controls described (e.g. shifter, clutch, steering wheel) are related to certain types of target vehicles and not necessarily the same controls for others. For example, many automobiles have automatic transmissions and, therefore, do not have a clutch. In another example, an airplane does not have rear-view mirrors, shifters, clutches, etc. Likewise, a truck driving simulator has rear-view mirrors, shifters, clutches, but does not have ailerons, thrust, altitude gauges, etc.

Referring to FIGS. 1 through 5, perspective views of a training system 10 are shown. The training system 10 is supported and/or housed by/in a cabinet 8 and in some embodiments, the cabinet moves (provides motion) in either the front/rear direction or both the front/rear direction and sideways direction as, for example, shown in U.S. Pat. No. 9,852,650 issued Dec. 26, 2017, which has been included by reference. The training system 10 provides life-like training without or before operation of the target vehicle, in this example a vehicle such as a truck or an automobile. Simulated rear view mirrors displays 42/43/44 are implemented as discrete display devices (as shown) or as part of another display (not shown for brevity and clarity reasons).

Figure 2:
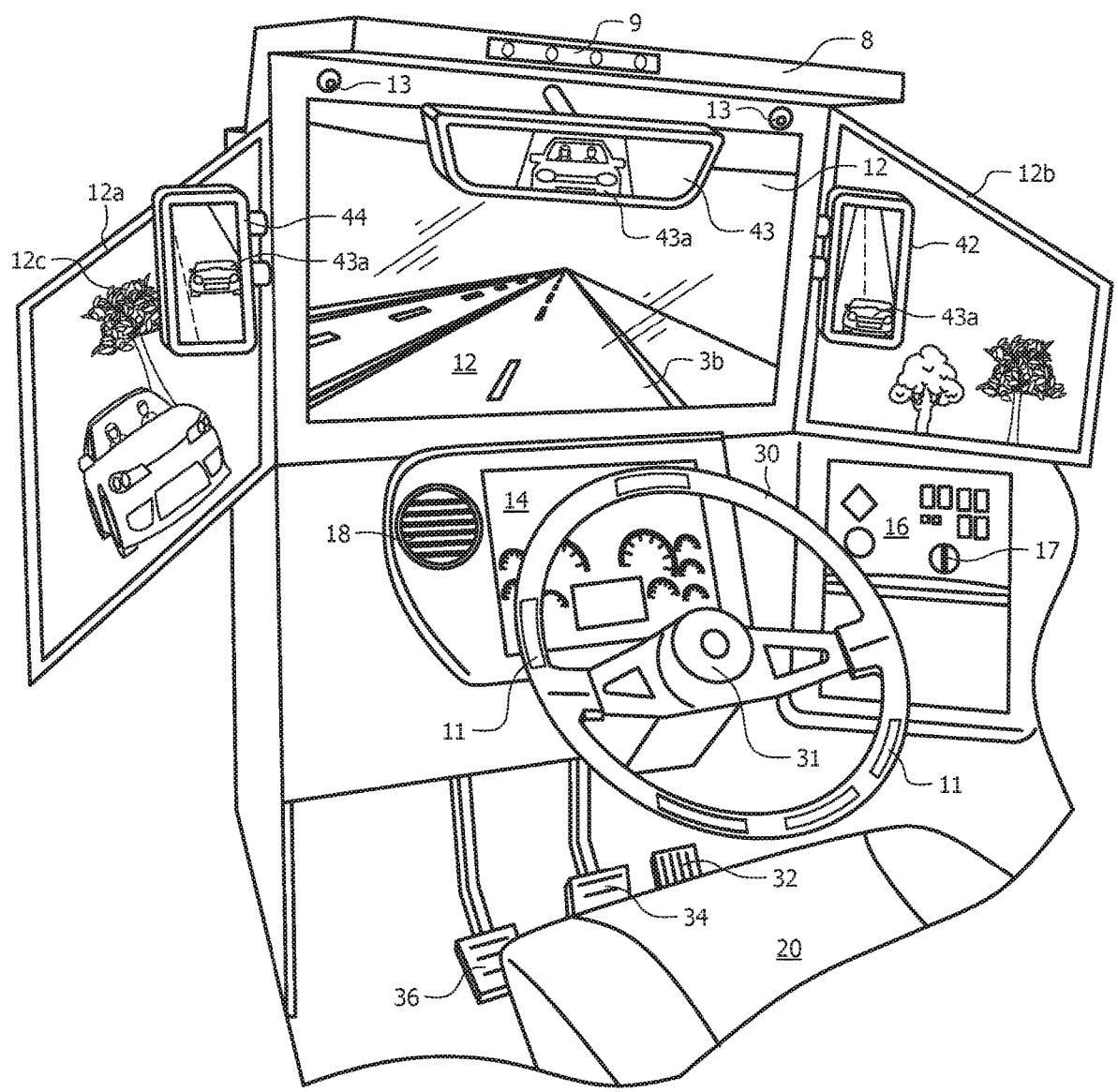
FIG. 2 illustrates a second perspective view of a training system.

As shown in FIG. 2, the exemplary training system 10 has a windshield display 12 on which a simulated driving situation is presented as the trainee 5 would see through the windshield of the target vehicle. The windshield display 12 shows, for example, the road being driven upon, the grade of the road, obstacles such as other vehicles, trees, parked cars, pot holes, etc. In some training scenarios, the windshield is fogged or distorted by simulated weather conditions such as rain, snow (as in FIG. 1), sleet, etc.

For improved realism, in some embodiments, images 12c of cars and other objects as they are being passed by the simulated vehicle are shown (motion) on a left window display 12A and/or a right window display 12B.

The trainee 5 typically sits on a seat 20 that, preferably, though not required, mimics a seat of the target vehicle. The trainee has controls similar to those in the target vehicle such as a steering wheel 30, horn 31, gas pedal 32, brake pedal 34, clutch 36 (see FIG. 2), and shifter having a shifter shaft 99 and a shifter handle 98 and shifter sub-system 80. The shifter subsystem is often covered with a boot 84 to keep dust, liquids, etc from damaging the working components.

In a preferred embodiment, though not required, the steering wheel 30 and shifter handle 98 have skin response sensors 11/33 that detect if and when the trainee 5 is grasping the steering wheel 30 and/or shifter handle 98. The skin response sensors 11/33 are any known sensor such as a mechanical switch or switches, capacitive or resistive detectors, etc. In some embodiments, the skin response sensors 11/33 measure a heart rate (e.g. beats per minute) and/or a galvanic skin response of the trainee, both being an indicator of stress in the trainee 5.

In some embodiments, the position of the trainee's hands is determined by the camera(s) 13 or a sensor array in conjunction with or instead of the skin response sensors 11/33.

In a position similar to that of a dashboard of the target vehicle is a dashboard (e.g. dashboard display) 14. The dashboard display 14 contains images and indicators that inform the trainee of various target vehicle and external conditions such as speed, engine speed (RPM), engine temperature, outside temperature, brake temperature, air pressure, oil pressure, etc. In some embodiments, the dashboard display 14 is fabricated from actual meters, indicators, etc, as in the target vehicle. In one embodiment, the dashboard display 14 is a graphics display on which the meters, indicators, etc of the target vehicle are displayed/simulated. In some embodiments, each sub-component of the dashboard display 14 is touch-sensitive. In such, the training system 10 prompts the trainee 5 to, for example, "touch" the tachometer, and the training system 10 receives a signal corresponding to the sub-component/icon that the trainee 5 touches. In embodiments, the dashboard display 14 is fabricated from actual meters, indicators, etc., and some or all sub-components have touch sensors such as pressure detectors or capacitive touch sensors, etc.

In some embodiments, one or more discrete side-positioned, rear-view mirror displays 42/44 are provided. In other embodiments, one or more side-positioned, rear view mirror image areas are reserved as part of the windshield display 12. The side-positioned, rear-view mirror displays 42/44 display a simulated view of what is visible to the trainee 5 such as vehicles being passed and/or approaching vehicles. In some embodiments, the side-positioned, rear-view mirror displays 42/44 simulate views of objects as they would appear in a true mirror, simulating concave or convex mirrors as appropriate. Additionally, in some embodiments, the images displayed on the side-positioned, rear-view mirror displays 42/44 includes simulated mirror imperfections such as dirt, rain drops, etc, as often occurs in real life.

In the past, such rear-view mirror displays 42/44 were static, in that, the image displayed showed one view of what is behind the trainee 5, independent of the location of the trainee's head and eyes. There are many scenarios when a driver, and hence the trainee 5, needs to position their head so that they are able to see certain aspects of what is behind the (simulated) vehicle. For example, it is often required that the driver (hence trainee 5) looking out the left mirror 44 move their head in away from the driver side window to make sure nothing is in the left lane or move their head toward the driver side window to view the status and position of the left truck wheels to better judge position, for example, within the lane or to avoid objects while backing up.

In recent years, technology has become available that will detect the spatial location of objects such as a person's arms, legs, head, torso, etc. To detect the location of the trainee's head and eyes for adjustment of rear view mirror images, the training system 10 includes a camera 13 and/or a sensor array 9 for detecting, at least, the location of the trainee's head. By analyzing data from the camera 13 and/or the sensor array 9, the training system 10 has knowledge of the position of the trainee's head and eyes with respect to the simulator's cab and with respect to each of the rear view mirror displays 42/43/44. An example of such a sensor array 9 and analysis technology is Kinect® manufactured by Microsoft®. In this technology, the sensor is a sensor array 9 including, for example, cameras, depth sensors, IR sensors, and voice sensors. In some embodiments, the sensor array 9 and analysis software are enabled to provide facial recognition, 3D construction, distances, facial expression analysis, body measurements (temperature, pulse rate, etc.). For automation of the side-positioned, rear-view mirror displays 42/44; the camera 13, the sensor array 9 and associated analysis software deliver a measurement of the position of the trainee 5, an in particular, the trainee's head, without the need to make direct connections to the trainee 5. Although originally designed for a game console (Xbox 360®), Kinect®, provides full-body 3D motion capture, facial recognition and voice recognition. An array of microphones also provides for acoustic source localization and ambient noise suppression. Kinect® is disclosed as an enablement of the present invention and any type of position recognition system is anticipated to provide some or all of the features disclosed here within. For example, in some embodiments, the sensor array 9 is one or more ultrasonic distance detection devices for determining the trainee's 5 position relative to one or more side-positioned, rear-view mirror displays 42/44, etc.

The training system 10 utilizes the sensor array 9 and analysis software in several ways to provide a more accurate simulation. For example, when the trainee 5 looks at the rear view mirror displays 42/44, the location and position of the trainee's head is determined using data from the sensor array 9 and the image in the rear view mirror displays 42/44 is adjusted to correspond to what the trainee 5 would be viewing from a perspective based on the angle and distance between the trainee's head and the rear view mirror displays 42/44. For example, as the trainee 5 positions their head closer to the rear view mirror displays 42/44, the display within the rear view mirror displays 42/44 is changed to reflect that distance, for example, zooming out on the content that is being displayed. As the trainee 5 shifts their head to the right or left, the image displayed in the rear view mirror displays 42/44 pans across a virtual image segment of a wide-view of what is in the rear of the simulation, showing, for example, the side of the simulated vehicle from one perspective and details of vehicles or guardrails that the simulated vehicle is passing in another perspective. In this way, the image in the mirror corresponds to the spatial position of the trainee's head (and therefore, eyes) and the trainee 5 learns how to reposition their head (and eyes) to see particular areas of the rear view that are important while, for example, moving forward within a lane or backing into a loading ramp. In another example, the cameras 13 and/or the sensor array 9 detect head and eye movement which is analyzed, in some embodiments along with other sensor data, to determine a stress level of the trainee 5. For example, when the stress level of the trainee 5 is high, the trainee 5 often moves their head left/right often, sometime nervous twitches begin, under extreme stress, the eyes of the trainee 5 might dilate and the skin tone of the trainee 5 pales.

Note that the particular sensor array 9 described is an example and any type of sensor and detection software is anticipated to determine the location of the trainee's head with respect to the rear view mirror displays 42/44/43; including infrared sensors, ultrasonic sensors, cameras, etc.

In some embodiments, a center-mounted rear-view mirror display 43 is also provided (not always present in trucks). When provided, the center-mounted rear-view mirror display 43 shows a simulated view of what is visible to the trainee 5 such as approaching vehicles and/or oncoming vehicles. As above, in some embodiments, the center-mounted rear-view mirror display 43 is also augmented by the position of the trainee 5 to better simulate what is viewed in the center-mounted rear-view mirror display as the trainee 5 repositions their head and eyes.

In some embodiments, an information console 16 is provided. The information console 16 does not necessarily simulate something from the target vehicle. Instead, the information console 16 presents menus, status information, and auxiliary information to the trainee 5 and accepts inputs such as scenario selection, study chapter selection, login data, etc.

In some embodiments, an audio system 18 is provided to enhance realism and provide simulations of sounds that are normally heard when operating the target vehicle such as engine noise, tire noise, other vehicles, rain or sleet hitting the target vehicle, emergency vehicles, sounds of a collision, etc.

In some embodiments, one or more sensor arrays 9 and/or cameras 13 are provided to detect various aspects of the trainee 5 such as position upon the seat 20, head angle, attention, drowsiness and where the trainee is looking. This information is used, for example, to make sure the trainee is properly performing the task at hand. The one or more sensor arrays 9 and/or cameras 13 include, for example, cameras, light detectors, ultrasonic transducers, or any other detector as known in the industry. The one or more sensor arrays 9 and/or cameras 13 are coupled to the computer 100 (see FIG. 9). The computer 100 analyzes images/inputs from the one or more sensor arrays 9 and/or cameras 13 to determine, for example, what the trainee 5 is doing, where the trainee 5 is looking, and the position/location of the trainee's head, flesh tone of the trainee 5, sweat on the skin of the trainee 5. In some embodiments, the sensor data is used to provide feedback to the trainee 5 and evaluate the trainee's abilities. For example, the camera(s) 13 are used to determine if the trainee 5 looked in the right rear view mirror display 42 before changing lanes and appropriate feedback is provided.

As discussed, there are various anticipated sources for determining a stress level of the trainee 5. For one, when the trainee 5 is touching the steering wheel 30 and/or shifter handle 98, skin response sensors 11 in the steering wheel 30 and/or skin response sensors 33 in the shifter handle 98 measure heart rate (e.g. beats per minute) and/or galvanic skin response. Further, the cameras 13 and sensor array 9 also provide inputs as to the stress level of the trainee 5. For example, the cameras 13 are able to determine skin temperature, sweat levels, and skin color. By monitoring skin temperature, sweating, and/or skin color, software determines the stress level of the trainee 5.

The training system 10 is equipped with one or more mechanisms for measuring the instantaneous stress and these mechanisms provide for individual differences when compared to a baseline stress level for the trainee 5. For example, both heart rate variability (HRV) and galvanic skin response (GSR) are measured on the driver in the simulation. Changes in these two measurements during a simulation exercise indicate that the driver is experiencing higher or lower levels of stress. In some embodiments, a baseline instantaneous stress level is saved as a user parameter in the user information 120 and used as a baseline in subsequent simulations while in some embodiments, a baseline instantaneous stress level is calculated when the trainee 5 begins a simulation exercise.

Having a calculation of instantaneous stress along with other parameters such as the level of stress expected for the current simulation segment, historical data for the trainee 5, historical data for all trainees 5, medical recommendations, etc., training system 10 continuously throttles the amount of stress delivered by the training system 10. In the past, simple systems merely changed the rate of presentation of the simulation, either faster or slower. Such changes in rate are artificial, like watching a movie at a faster playback speed. Movements become unreal, like watching a Charlie Chaplin movie. Such unreal movement is likely to further contribute to frustration and stress.

Instead, the training system 10 modifies the training exercise and/or the environment to provide conditions that lead to an improved level of stress (either increasing the instantaneous stress level or decreasing instantaneous stress level). As shown in FIG. 1, the road ahead is curvy, snowflakes are falling, and looking in the rear view mirror 43, a trailing vehicle 43*a* is very close, tailgating. All of this causes increased stress for the trainee 5. As the instantaneous level of stress of the trainee 5 is measured and plotted, if the instantaneous level of stress of the trainee 5 is over a high-stress threshold or a high-stress threshold percentage increase is detected, then a stress-change feature is selected in the simulation is modified to reduce the level of stress.

Although there is no restriction on how the stress-change feature is selected, in some embodiments, the stress-change feature is selected randomly, in some embodiments, the stress-change feature is selected in a predetermined order, while in some embodiments, the stress-change feature is selected based upon the severity of the instantaneous stress level (e.g., certain stress-change features are rated for very high instantaneous stress levels while some stress-change features are rated for lower instantaneous stress levels).

Figure 4:
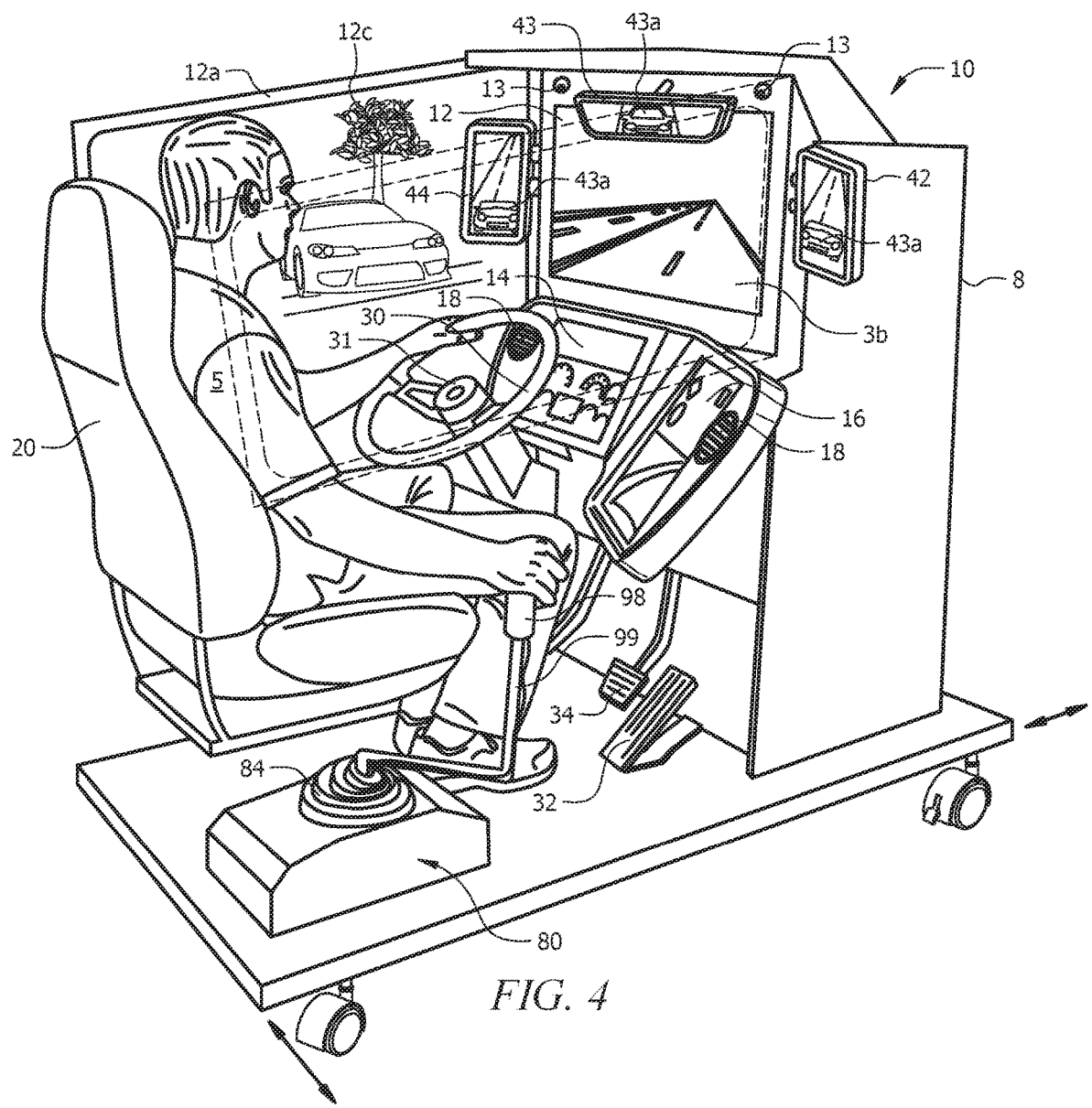
FIG. 4 illustrates a fourth perspective view of a training system with a second exemplary step in reducing stress.
Figure 5:
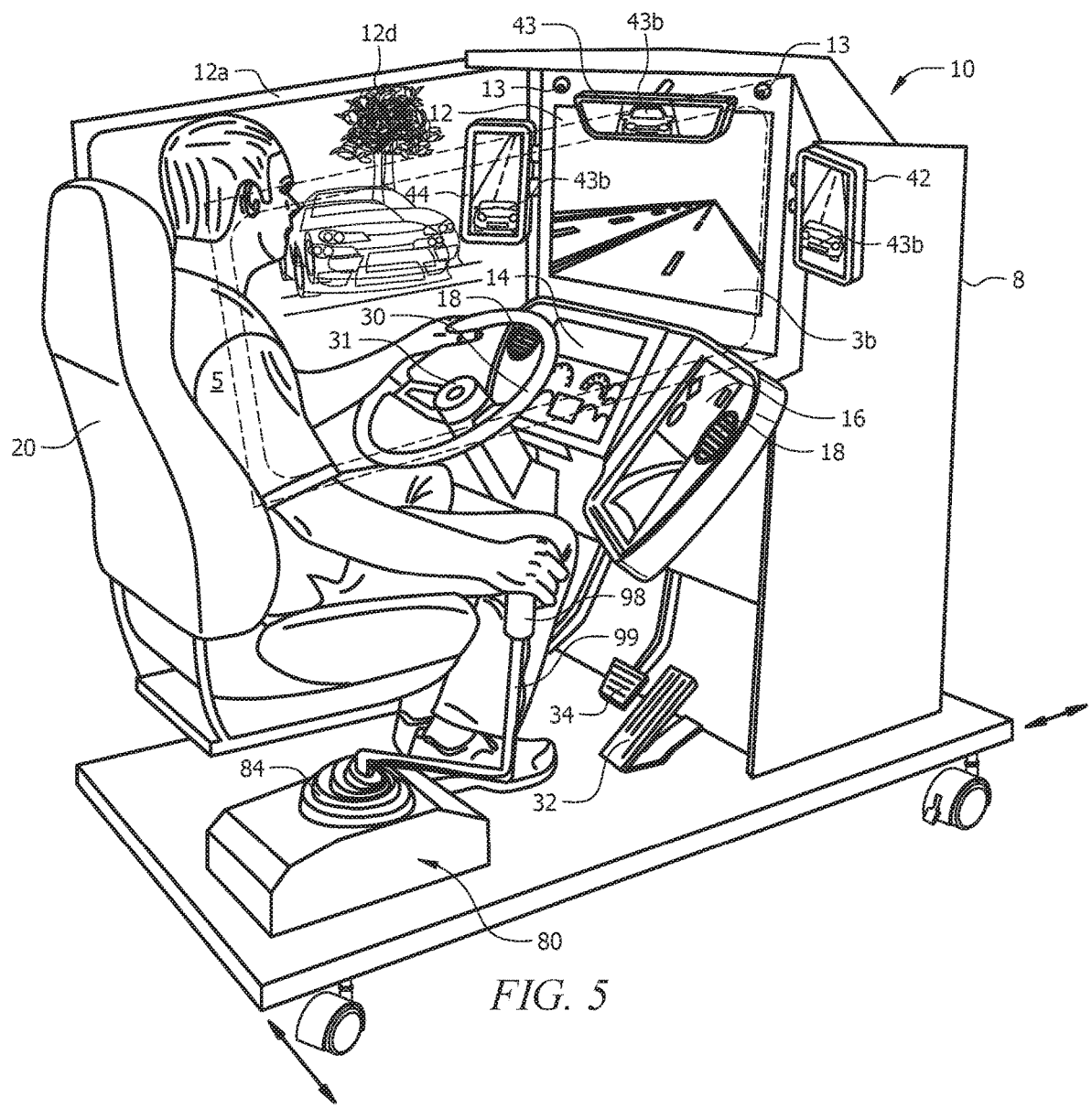
FIG. 5 illustrates a fifth perspective view of a training system with a fourth exemplary step in reducing stress.

For example, the simulation begins as shown in FIG. 1: the road ahead is a curvy road 3*a*, snow 4 is falling, a trailing vehicle 43*a* is tailgating, and scenery is passing by quickly in the side windows 12*a*/12*b* indicating rapid movement of the simulated vehicle. This is a very stressful scenario. As the instantaneous stress of the trainee 5 is continuously measured and plotted, as the instantaneous stress of the trainee 5 increases, a stress-change feature is selected in the current scenario of the simulation and the simulation is modified as shown in FIGS. 3-5.

Figure 3:
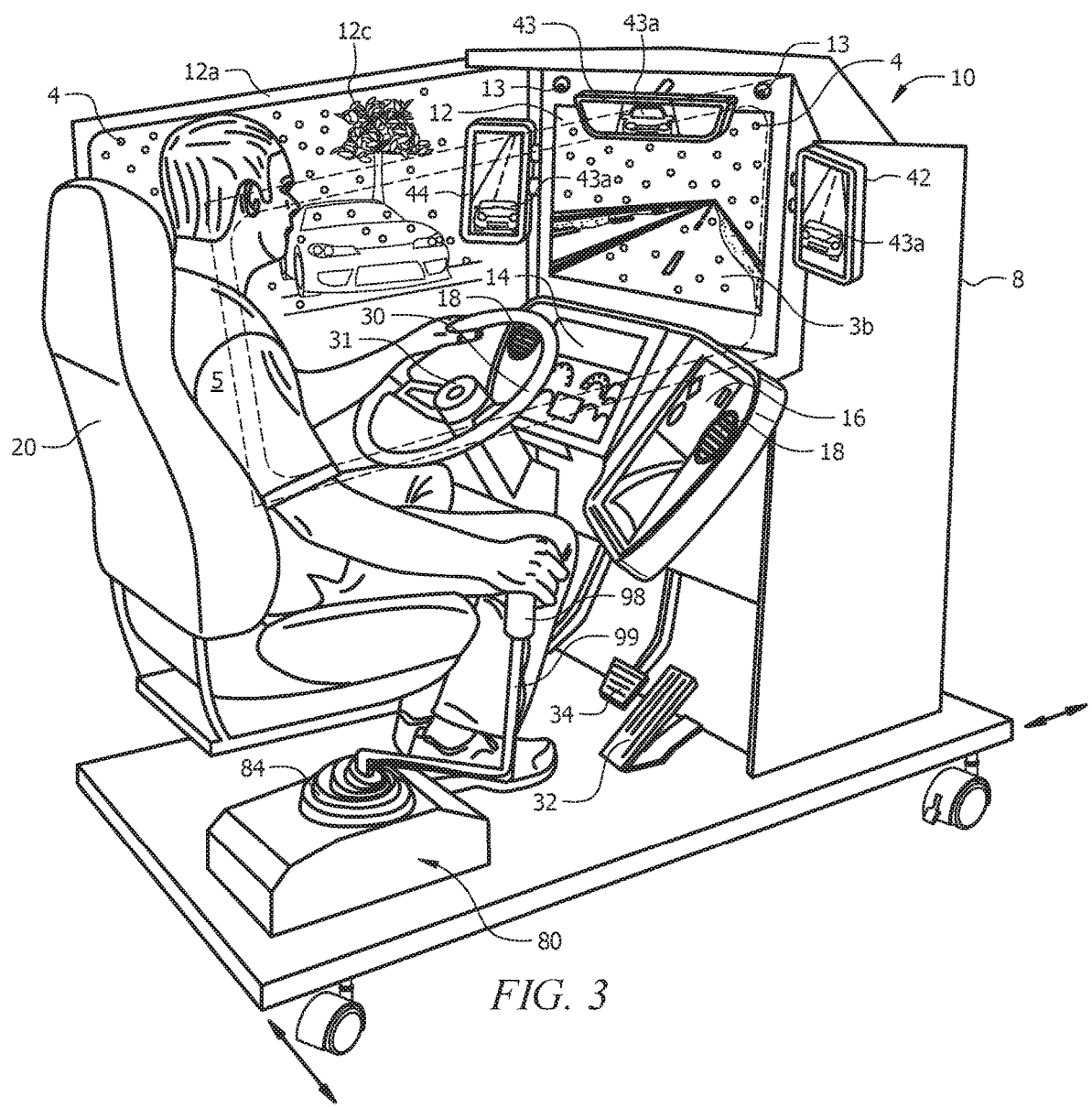
FIG. 3 illustrates a third perspective view of a training system with a first exemplary step in reducing stress.

In FIG. 3, the stress-change feature selected is steering requirements and the simulation is modified so that the road ahead is changed to be a straight road 3*b* instead of a curvy road 3*a*, so the trainee 5 doesn't need to worry about making turns in the snow 4 with the trailing vehicle 43*a* tailgating.

After the simulation is modified to straighten the curvy road 3*a*, the instantaneous level of stress of the trainee 5 is continuously measured and plotted, if the instantaneous level of stress of the trainee 5 is still over the high-stress threshold or the high-stress threshold percentage increase, then another stress-change feature is selected in the current scenario of the simulation and the simulation is further modified to reduce the level of stress. In FIG. 4, the road ahead remains a straight road 3*b* and the stress-change feature that was selected is weather conditions, hence, it is no longer snowing. The trainee 5 doesn't need to worry about making turns or maneuvering in the snow with the trailing vehicle 43*a* tailgating.

Again, as the instantaneous level of stress of the trainee 5 is continuously measured and plotted, if the instantaneous level of stress of the trainee 5 is still over the high-stress threshold or the high-stress threshold percentage increase, then a stress-change feature is selected in the current scenario of the simulation and the simulation is further modified to reduce the level of stress. In this example, the stress-change feature selected is distractions. For example, the images 12*c* in the side windows 12A/12B are change to blurry images 12*d* as in FIG. 5. By showing of the blurry images 12*d*, the stress level of the trainee 5 is reduced as there are less side distractions and less feeling of moving fast.

Although, not shown for clarity reasons, in some embodiments, a stress-change feature is selected in the current scenario of the simulation as aggressive drivers. In this, the view displayed in the rear view mirror displays 42/43/44 is changed to show the trailing vehicle 43*b* back off to a safe distance. Now, the trainee 5 doesn't have to worry about being hit by the trailing vehicle 43*b*.

Note that any combination and/or order of stress-change features and resulting modifications to the simulation are anticipated including those described above and removing or changing other parts of the simulation including, but not limited to, removing pedestrians, changing the grade of the road, widening the road, increasing lighting/visibility, quieting simulated noise from the road/vehicle, reducing traffic, removing vehicles that are driving poorly, improving weather conditions, providing a rest station/pull-off, keeping traffic lights green, lowering the brightness of the dashboard display 14, reducing X/Y/Z movement of the training system 10, etc.

The inverse of the above scenarios also works. As it is known that if stress levels are too low, the trainee 5 is not challenged substantially, boredom sets in and learning stops. Therefore, as the instantaneous level of stress of the trainee 5 is continuously measured and plotted, if the instantaneous level of stress of the trainee 5 is lower that a learning stress threshold or a learning stress threshold percentage decrease, then a stress-change feature is selected in the current scenario of the simulation and the simulation is further modified to increase the level of stress. For example, the blurry images 12*d* in the side windows 12A/12B as in FIG. 5 are change to images 12*c* that are not blurry as in FIGS. 1-4. In a similar way, stress levels are further increased by any combination of the elements (snow 4, trailing vehicle 43*b* tailgating, curvy road 3*a*) or by adding or changing other parts of the simulation including, but not limited to, adding pedestrians, increasing the grade of the road, narrowing the road, decreasing lighting/visibility, increasing simulated noise from the road/vehicle, increasing traffic, adding one or more vehicles that are driving poorly, worsening of weather conditions, changing traffic lights to read, increasing the brightness of the dashboard display 14, increasing X/Y/Z movement of the training system 10, etc.

If, after all known ways to increase the stress level of the trainee 5 are implemented, if the instantaneous level of stress of the trainee 5 is measured and plotted and is still over the high-stress threshold or the high-stress threshold percentage increase is detected, further action is taken such as stopping the simulation and notifying an instructor.

In a similar way, if the instantaneous level of stress of the trainee 5 is measured and plotted and is under a learning threshold or a learning threshold percentage decrease is detected, the opposite steps to those of FIGS. 3-5 are taken (e.g. present a more challenging course with curves as in FIG. 3, indicate that snow is falling as in FIGS. 3 and 4, show a tailgater in the rear view mirror 43 . . . ).

FIG. 3 shows a stress-change feature in the current scenario of the simulation that includes changing the challenge of the scenario, in this example, by changing the road ahead as displayed on the windshield display 12 from a curvy road 3a to a straight road 3b or vice versa, though other difficultly changes are anticipated such as widening the roadway, removing traffic or limiting the number of other vehicles, removing road side distractions such as pedestrians and cyclists, etc.

FIG. 4 shows another stress-change feature in the current scenario of the simulation that includes changing the challenge of the scenario, in this example, by removing or adding an element of weather (snow), though other weather-related changes are anticipated such as rain, lightning, high-winds, sleet, ice-covered roads, wet roads, etc.

FIG. 5 shows another stress-change feature in the current scenario of the simulation that includes changing the visibility of objects passing by in the side windows 12A/12B, in this example, by blurring/focusing the side windows 12A/12B to remove/add this distraction to the driver.

In another scenario, another stress-change feature in the current scenario of the simulation includes changing the mirror views to indicate that the trailing vehicle 43b is no longer tailgating and is now maintaining a safe distance.

Note that the present application places no restriction as to the order in which stress-change feature and resulting steps are taken. Again, if the instantaneous level of stress of the trainee 5 is measured and plotted and the instantaneous stress is under a learning threshold or a learning threshold percentage decrease is detected, the opposite steps to those of FIGS. 3-5 are taken (e.g. present a more challenging course with curves as in FIG. 3, indicate that snow is falling as in FIGS. 3 and 4, show a tailgater in the rear view mirror 43 . . . ), as it has been shown that a certain amount of stress improves learning and retention.

Figure 6:
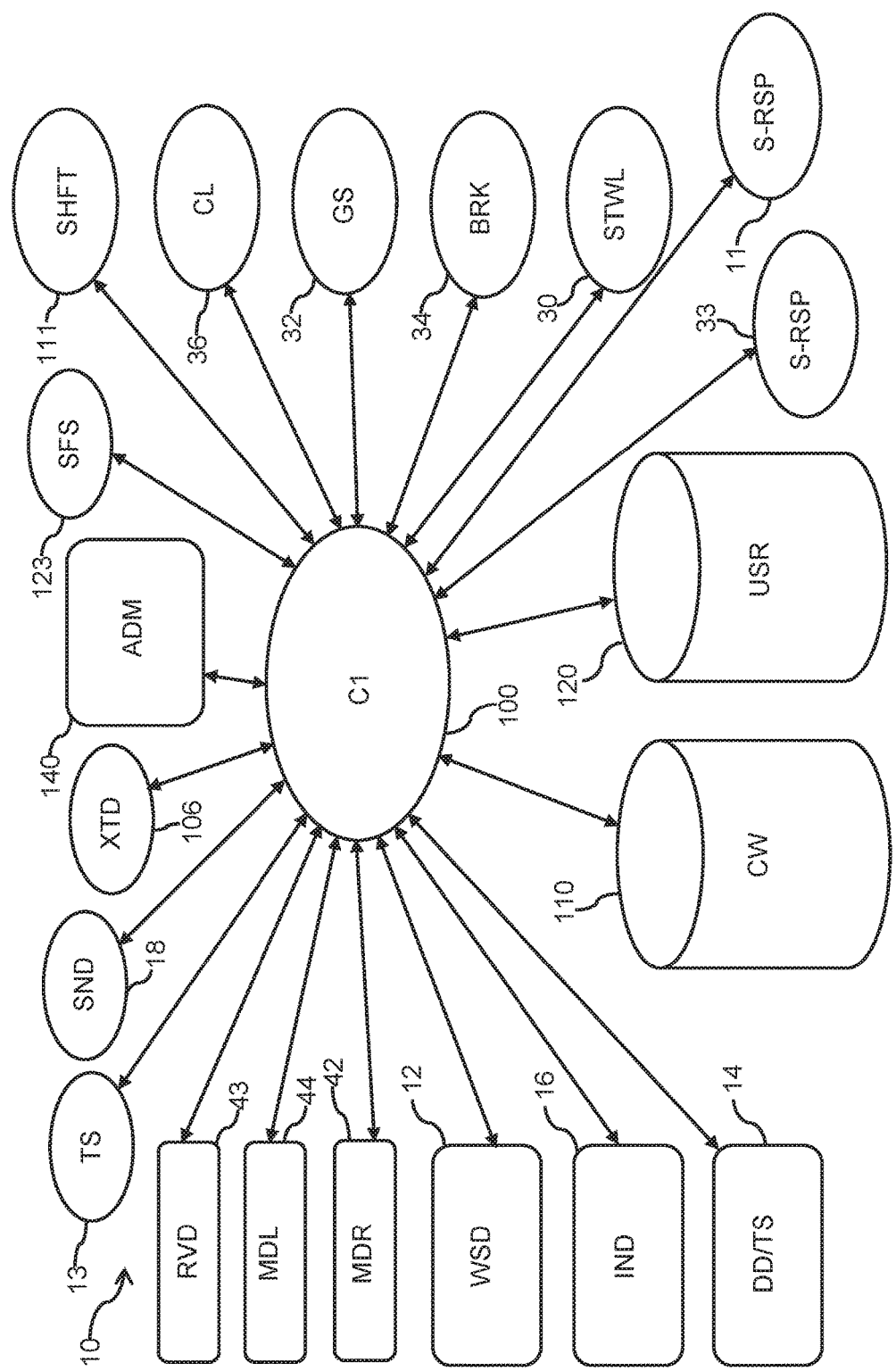
FIG. 6 illustrates a schematic view of an exemplary training system.

Referring to FIG. 6, a schematic view of an exemplary training system 10 is shown. As discussed prior, it is anticipated that one or more of the following described features is or is not present in all embodiments. For example, in some embodiments, there is no trainee sensor (e.g. no camera 13) that determines where the trainee 5 is looking, etc.

Central to the training system 10 is a computer 100. Many different types of computers 100 are anticipated such as personal computers, dedicated computers and server computers. It is anticipated that computers 100 of one training system 10 are connected by local or wide area networks to other training systems 10 and/or to central data collection and control systems (not shown). In some embodiments, the computer has a motherboard with multiple PCI-Ex16 slots that provide multiple simulator display channels with 2D and/or 3D capability. A video processor card is optionally installed in each of these slots. The video cards typically display the simulation in multi channel mode with low transient delay times. It is anticipated, though not required, that a single image generator (single motherboard computer) can drive multiple displays. Although any number of display channels is anticipated, the training system typically is configured with from 3 to 8 real time interactive screens 12/14/16/42/43/44/12A/12B.

The computer 100 includes, in some embodiments, a display device or terminal device 140. This device 140 has a display screen, a keyboard and/or a touch screen and is primarily used by an administrator to operate the computer 100, for example, performing backups and other system administration function. In some embodiments, these functions are performed using one or more of the other components/displays 12/14/16.

The computer 100 also includes persistent storage 110/120 such as hard drives, flash memory, etc. for storage of, for example, courseware 110 and user information 120. In a preferred embodiment, the persistent storage 110/120 is one or more hard drives or solid-state drives. In some embodiments, the storage 110/120 is a raid system to provide more reliable data storage.

Interfaced to the computer 100 are several components of the training system 10. The windshield display 12, dashboard display 14 (e.g. dashboard graphics display and touch screen) and information console 16 are all interfaced to the computer 100 as known in the industry. The rear-view mirror displays 42/43/44 (when present) are also interfaced to the computer 100 as known in the industry. All specialized hardware devices such as the skin response sensors 33 in the shifter handle (also the X-position, Y-position, switch status not shown for brevity reasons), clutch 36 (position and force), gas pedal 32 (position and force), brake pedal 34 (position and force) and steering wheel 30 (rotation and touch) are also interfaced to the computer 100 as known in the industry. It is preferred that some or all of such interfaces are bi-directional to provide control of the device (e.g. vary the counter-force of the brake pedal 34 or gates of the shifter sub-system 80) and to receive feedback from the device (e.g. sufficient pressure was applied to the brake pedal 34, hands are on the steering wheel 30 or the trainee 5 successfully shifted from first gear into second gear).

In embodiments that have trainee sensors such as cameras 13, etc., the trainee sensors (e.g. cameras 13) are interfaced to the computer 100 as known in the industry.

In embodiments that have skin response sensors 11/33 (e.g. on the steering wheel 30 or on shifter handle 98), the skin response sensors 11/33 are interfaced to the computer 100 as known in the industry.

In embodiments that have shifter force sensors 123 (on shifter shaft 99, the shifter force sensors 123 are interfaced to the computer 100 as known in the industry.

In some embodiments, one or more biometric sensors 15 are interfaced to the computer 100. The skin response sensors 11/33 sense, for example, fingerprints, retina characteristics, facial characteristics, pulse rate, galvanic skin response, etc., of the trainee 5 who is using the training system 10 to make sure the training and results correspond to the correct trainee 5. Such skin response sensors 11/33 are used to determine an instantaneous stress level of the trainee 5. In some embodiments, the skin response sensors 11/33 are used to provide immediate feedback or to stop a simulation should there be a threat of bodily harm or harm to the training system 10. In some embodiments, the skin response sensors 11/33 are also used to identify the trainee 5, thereby preventing the trainee 5 from intentionally or unintentionally scoring/learning for another trainee 5.

In embodiments having a sound system 18, the sound system 18 is interfaced to the computer 100 as known in the industry such as audio outputs connected to amplifiers and speakers, TOSLINK, USB, etc.

In embodiments having a transmission transducer 106, the transmission transducer 106 is interfaced to the computer 100 as known in the industry such as through audio outputs connected to amplifiers and speakers, TOSLINK, USB, etc or over a local area network.

Figure 7:
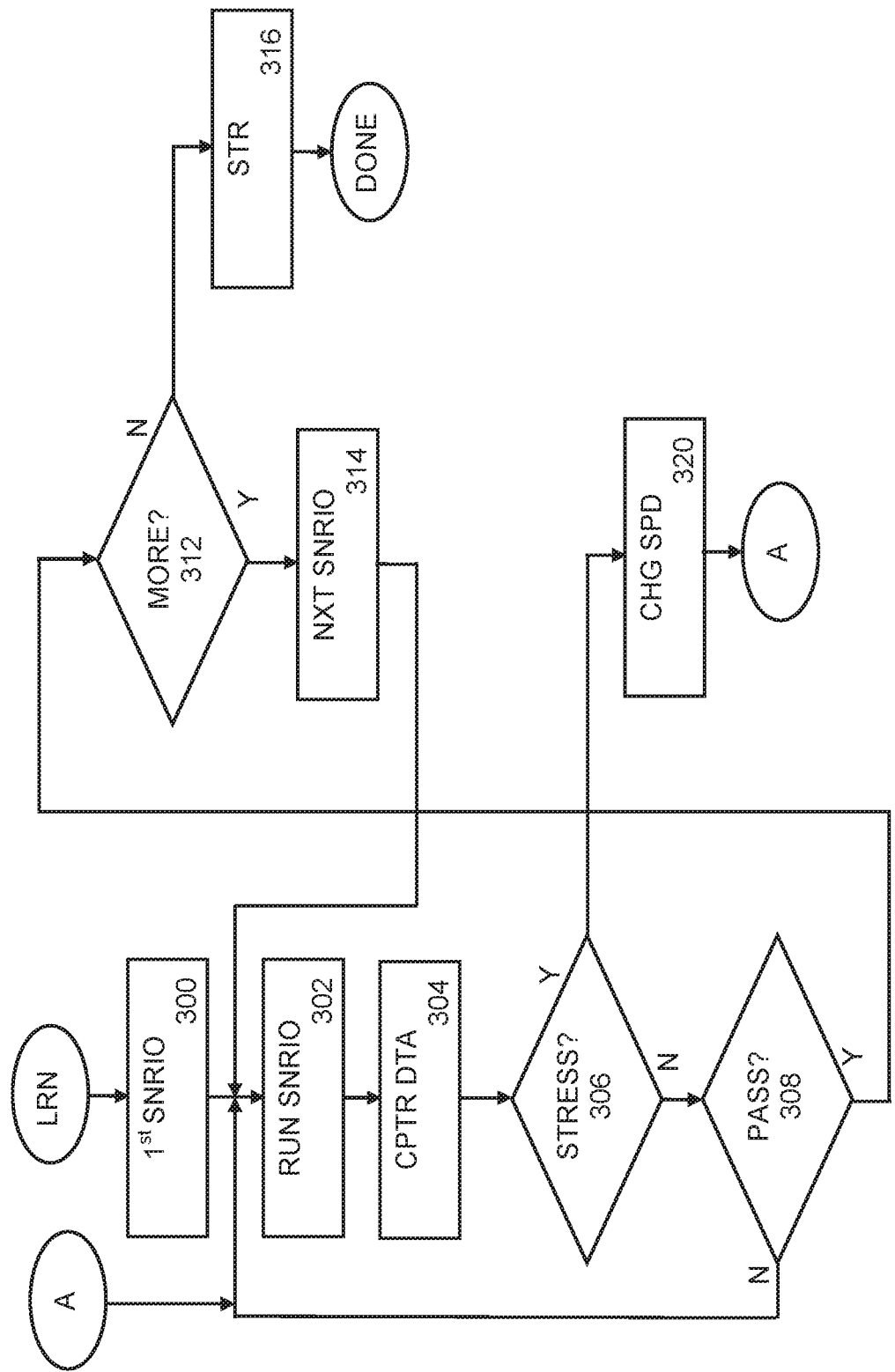
FIG. 7 illustrates a flow chart of the prior art.

Referring to FIG. 7, a flow chart of a training model of the prior art is shown. This represents either one segment of a training method or the entire training method of the prior art.

Flow begins with a first scenario/segment is selected 300 then run 302 at a standard speed and data is captured 304 during and/or after the scenario/segment is run. An example of a simple scenario/segment is a simulation of driving down a road way, approaching an unmarked intersection and a vehicle pulls out from the intersection into the path of the trainee 5. If the captured data indicates a significant increase in stress 306 then the speed of the simulation is adjusted 320. In the prior art, changing of the speed of the simulation may help adjust stress levels of the trainee 5, but a slower presented simulation that was recorded to run at a higher speed will not appear to be real to the trainee 5 and will likely impact learning.

Data is analyzed to determine the performance of the trainee 5 in the given scenario/segment meets passing requirements (meets passing requirements 308). If not, the scenario/segment is repeated 302/304/306/308. If the trainee 5 meets passing requirements 308, it is determined if there are more scenarios/segments 312 for the trainee 5 (e.g. scenarios/segments are often grouped in chapters and the trainee 5 is finished when he/she complete a chapter, etc). If there are more scenarios/segments 312, the next scenario/segment is retrieved 314 and the above steps 302/304/306/308/312 are repeated until there are no more scenarios/segments planned for the trainee 5 and the captured data is stored 316 for progress analysis, grading, etc.

The methods of the prior art do not adapt to the trainee's 5 demonstrated abilities and/or stress levels, running scenarios/segments sequentially, independent of any progress that the trainee 5 has made. For example, in a set of scenarios/segments are crafted to teach defensive driving, offending vehicles are displayed moving into the path of the trainee 5. If the trainee 5 demonstrates excellent responses to each of the first few scenarios/segments, the latter scenarios/segments are still presented, often boring the trainee 5. In the trainee 5 shows signs of stress (e.g. increased heart rate, changes in galvanic skin response, pale skin), the prior art slows the presentation of the simulation, making the trainee 5 feel like they are watching a movie in slow motion and reducing realism.

Similarly, if the trainee 5 shows a weakness in a certain operation such as double-clutching, the prior art would only repeat the scenarios/segments until the trainee 5 is able to pass that segment. In the later situation, it is desirable to access other scenarios/segments that may have already been completed for extra training on the operation of which the trainee 5 is having difficulty. The prior art does not address such operation to adapt to the demonstrated abilities of the trainee 5.

Figure 8:
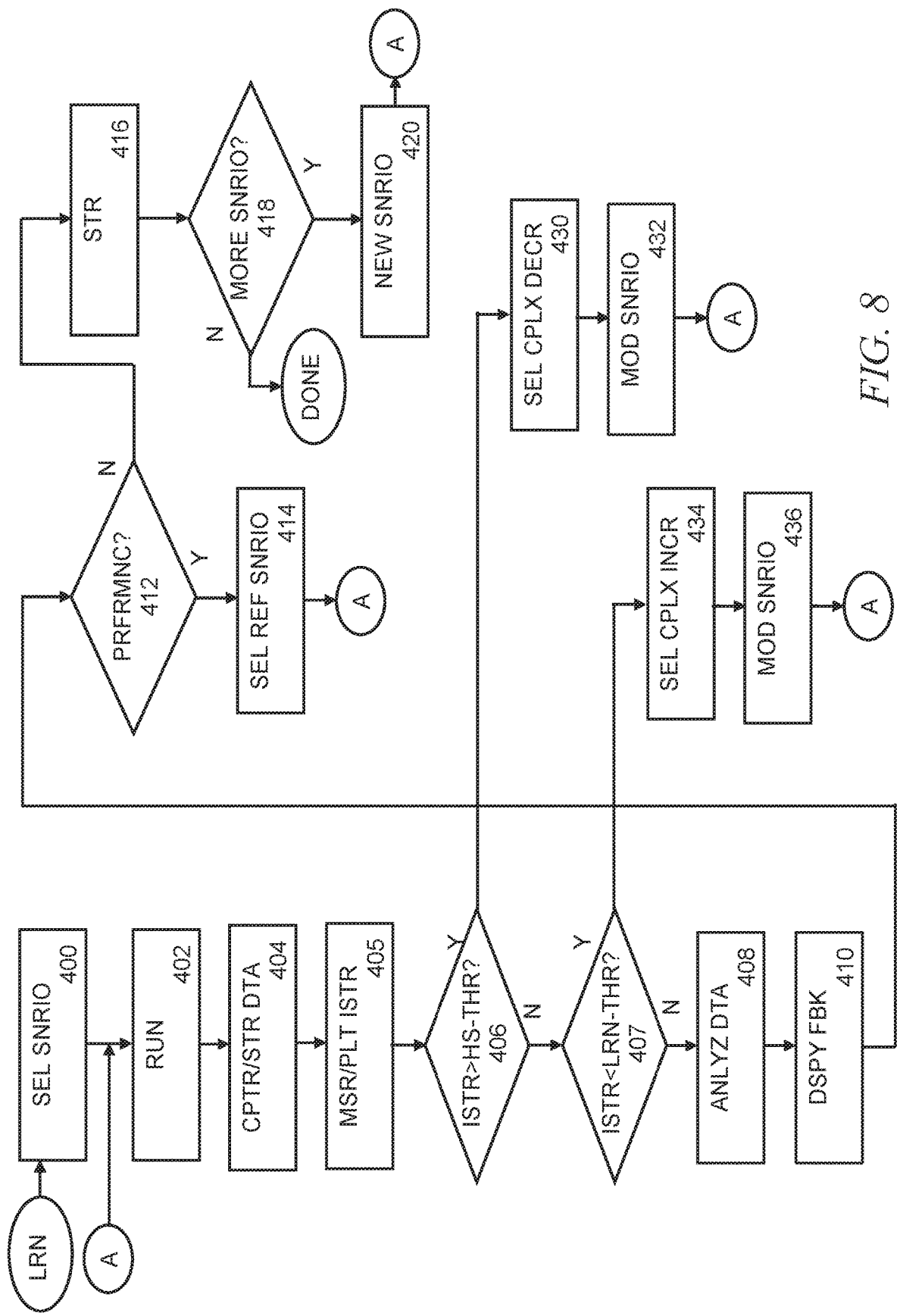
FIG. 8 illustrates a flow chart of changing scenarios based upon stress levels of the training system.

Referring to FIG. 8, a flow chart of the adaptive training system is shown. Typically, a chapter or portion of a training course (courseware 110) is presented in one session to the trainee 5. The methods disclosed monitor the demonstrated abilities (or lack thereof) and/or instantaneous stress levels of the trainee 5 and adapt the training course to such.

Flow begins by selecting 400 a first scenario/segment then the scenario/segment is run 402. Data is captured/analyzed/stored 404 during and/or after the scenario/segment is run. An example of a simple scenario/segment is a simulation of driving down a road way, approaching an unmarked intersection and a vehicle pulls out from the intersection into the path of the trainee 5. In some scenarios, the captured data indicates a major issue occurred such as the trainee 5 didn't apply the brakes fast enough (response time).

During the loop (or while the scenario/segment is running 402), the instantaneous level of stress of the trainee 5 is measured and plotted 405. The instantaneous level of stress is measured using, for example, the skin response sensors 11/33 that measure biometric parameters such as the pulse (heart rate) of the trainee 5, the galvanic skin response of the trainee 5, a skin temperature of the trainee 5, skin moisture of the trainee 5, oxygen concentrations in the blood of the trainee 5, etc. Further, in some embodiments, the trainee 5 is monitored by other sensors such as the camera(s) 13 or a sensor array 9 to measure posture, skin color, skin moisture (e.g. sweat), head movements, etc., as instantaneous levels of stress are further detectable by certain eye movements, sweating, leaning forward, paling of the skin, etc.

The instantaneous level of stress of the trainee 5 is measured and plotted 405 to develop a normalized instantaneous level of stress over time, for example, during a low-stress scenario/segment. This provides a base-line level of stress of the individual trainee 5 for use in calculating changes in the instantaneous stress level of the trainee 5.

Now, while the scenario/segment is run 402 (or after the scenario/segment), the instantaneous level of stress of the trainee 5 is measured and plotted during. If the instantaneous level of stress (ISTR) remains over a high-stress threshold or over a high-stress threshold percentage increase 406 for a period of time, steps are taken to reduce the stress level by selecting 430 and applying 432 a stress-change feature that will reduce the complexity of the tasks at hand (e.g. as described above: straighten/widen roadway ahead, remove one or more weather conditions, remove pedestrians, cyclists, change from night to day, etc.) or by selecting 430 and applying 432 a stress-change feature that will reduce distractions (e.g. blurring the side windows 12A/12B). The steps typically include selecting 430 a stress-change feature that will reduce complexity and applying 432 that stress-change feature to the scenario/segment to operate the current scenario/segment without the complexity of that stress-change feature.

If, instead, the instantaneous level of stress (ISTR) remains under a learning threshold or under a learning threshold percentage decrease 407 for a period of time, steps are taken to increase the stress level by increasing the complexity of the tasks at hand by selecting 434 a stress-change feature 434 that will to increase/introduce (e.g. as described above: straighten/widen roadway ahead, remove one or more weather conditions, remove pedestrians, cyclists, change from night to day, etc.) or by increasing distractions (e.g. more activity and clearer side windows 12A/12B). The steps typically include selecting 434 a stress-change feature that will increase the complexity of the tasks at hand (and therefore, increase the instantaneous stress level) and applying 436 the stress-change feature to the scenario/segment so as to operate the simulation with the addition of that complexity.

If the instantaneous level of stress (ISTR) remains above the learning threshold or above the learning threshold percentage decrease 407 and below the high-stress threshold or below a high-stress threshold percentage increase 406, the data is analyzed 408 to determine the performance of the trainee 5 in the given scenario/segment and status is displayed 410 to the trainee 5 on one or more of the display devices 12/14/16. If the performance indicates that the trainee 5 didn't performed the task sufficiently 412, a new, refresher, scenario/segment is selected 414 and the above repeats. In some embodiments, the new scenario/segment is selected 414 based upon elements of the prior scenario/segment that were not adequately performed. Since adaptive training is provided, the method uses any existing or modified scenario/segment to fortify any elements of the prior scenario/segment that were not adequately performed. For example, if the trainee 5 avoided a collision but the trainee 5 didn't step on the clutch while applying the brakes, therefore stalling the engine, one or more scenarios/segments or chapters related to proper use of the clutch while braking are selected 414 to be presented to the trainee 5 either during the current session or during a future session.

If the trainee's 5 performance meets passing requirements 412, the data (e.g. results) are stored 416 for later reporting/analysis/grading. Next, if there are more scenarios/segments 418 for the trainee 5 (e.g. scenarios/segments are often grouped in chapters and the trainee 5 is finished when he/she complete a chapter, etc.), the next scenario/segment is retrieved 420 and the above steps 402-434 are repeated until there are no more scenarios/segments planned for the trainee 5.

Figure 9:
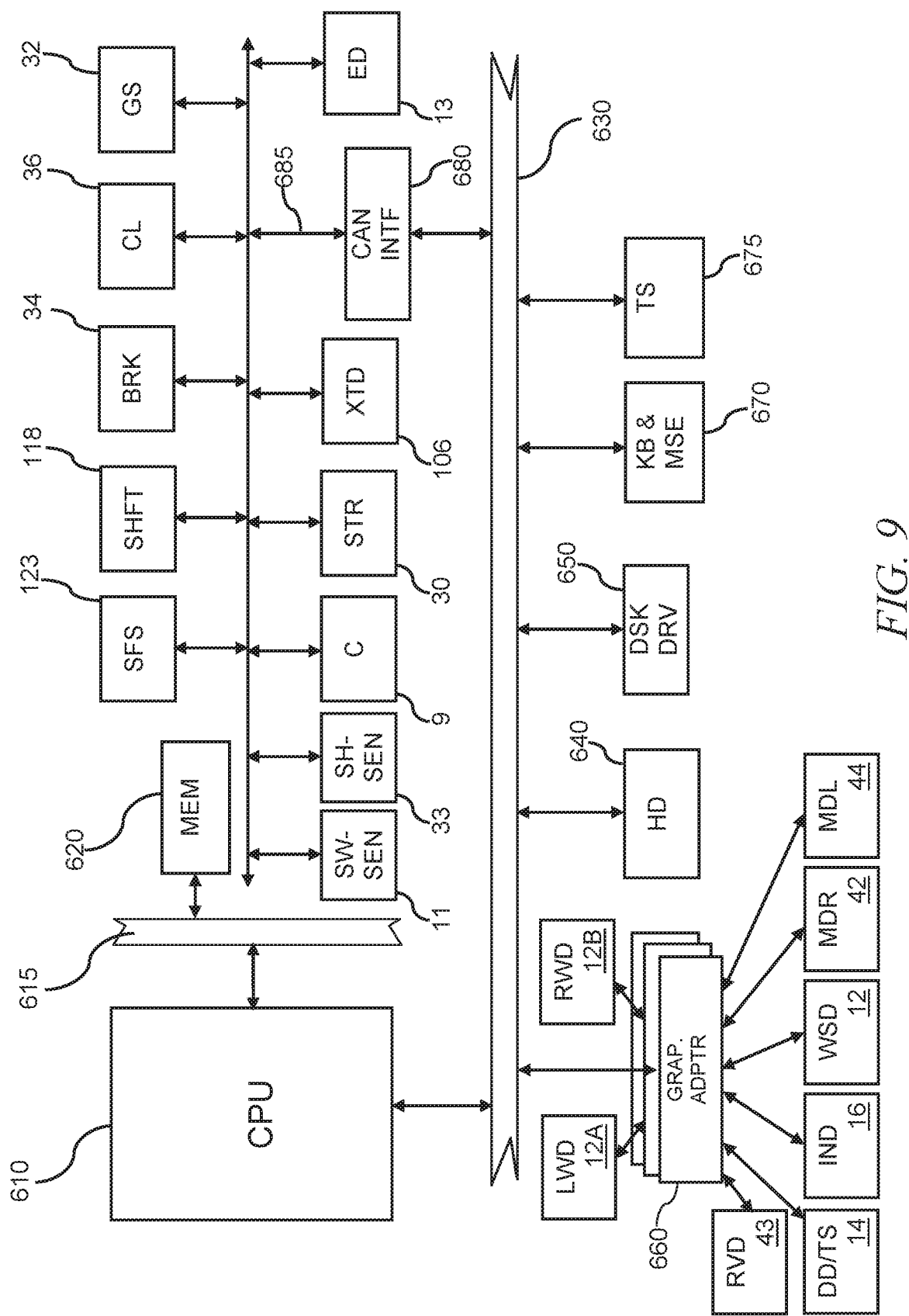
FIG. 9 illustrates a schematic view of a typical computer system.

Referring to FIG. 9, a schematic view of a typical computer 100 is shown. The exemplary computer 100 represents a typical computer system used as the heart of the training system 10. The example computer 100 is shown in its simplest form, having a single processor. Many different computer architectures are known that accomplish similar results in a similar fashion and the present invention is not limited in any way to any particular computer system. The present invention works well utilizing a single processor system, a multiple processor system where multiple processors share resources such as memory and storage, a multiple server system where several independent servers operate in parallel (perhaps having shared access to the data or any combination). In the example of FIG. 9, a processor 610 is provided to execute stored programs that are generally stored for execution within a memory 620. The processor 610 can be any processor or a group of processors. The memory 620 is connected to the processor in any way known in the industry such as by a memory bus 615 and the memory 620 is any memory 620 suitable for use with the selected processor 610, such as SRAM, DRAM, SDRAM, RDRAM, DDR, DDR-2, flash, etc.

Also connected to the processor 610 is a system bus 630 for connecting to peripheral subsystems such as a network interface (not shown), a persistent storage 640 (e.g. a hard disk, semiconductor storage such as flash, a raid system, etc.), a removable disk drive 650 (e.g. DVD), one or more graphics adapters 660, a keyboard/mouse 670 and/or one or more touch screen interfaces 675. The graphics adapter(s) 660 receives commands and display information from the system bus 630 and generates a display image that is displayed on one or more of the graphic display devices 12/14/16/42/43/44/12A/12B.

In general, the persistent storage 640 is typically used to store programs, executable code and data (e.g. courseware 110 and user information 120) persistently. For data security and reliability, in some embodiments, the persistent storage 640 is multiple disks or a raid system, etc. The removable disk drive 650 is often used to load CD/DVD/Blu-ray disks having programs, executable code and data onto the persistent storage 640. These peripherals are examples of input/output devices, persistent storage and removable media storage. Other examples of persistent storage include core memory, FRAM, flash memory, etc. Other examples of removable disk drives 650 include CDRW, DVD, DVD writeable, Blu-ray, compact flash, other removable flash media, floppy disk, etc. In some embodiments, other devices are connected to the system through the system bus 630 or with other input-output connections. Examples of these devices include printers; graphics tablets; joysticks; audio components; and communications adapters such as modems and Ethernet adapters.

Although there are many ways anticipated for connecting training system components 11/13/30/32/33/34/36/106/9/118/123 to the processor, one preferred interface is a bi-directional local area network such as Car Area Network (CAN) 685 connected to the bus 630 by a Car Area Network (CAN) interface 680 as known in the industry. Any connection scheme to the training system components 11/13/30/32/33/34/36/106/9/118/123 is anticipated including direct wiring, any local area network (e.g. Ethernet, CAN or VAN) and wireless (e.g. Bluetooth).

In embodiments having a sensor array 9, information from the sensor array 9 is read by the processor 610 and analyzed to provide various data such as the position of the trainee's head, the location of the trainee's head, the location of the trainee's hands/arms, the facial expressions of the trainee 5, the body temperature of the trainee's body, the pulse rate of the trainee's heart, etc.

As discussed above, the processor 610 reads various sensors 13/9/11/33 and monitors the camera(s) 13 and sensor arrays 9 and calculates the instantaneous stress (IST). For example, when the hands of the trainee 5 hold the steering wheel 30 and/or the shifter handle 98, skin response sensors 11/33 measure biometric values of the trainee 5 such as galvanic skin response, pulse rate, skin temperature. As these biometric values of several trainees 5 vary, in some embodiments, a baseline value for each value if read and the instantaneous stress (IST) is calculated as changes from the baseline values. For example, some people have a faster heart rate (e.g. 70 pulses per minute) and some have a lower heart rate (e.g. 60 pulses per minute). If an absolute value is used for determining the instantaneous stress (IST) from the heart rate, the person with the faster heart rate would already be biased toward higher stress. Instead, in some embodiments, a percentage increase (or decrease) from the baseline is used to determine instantaneous stress (IST). In this example, if the heart rate of the trainee 5 increases by 10, whether the baseline was 60 or 70, the increase is still greater than, say, 10%, and will indicate instantaneous stress (IST).

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A training system, the training system providing training on operation of a vehicle to a trainee, the training system comprising:
   a computer, the computer having a storage device;
   a plurality of training segments stored on the storage device and accessible by the computer;
   one or more graphics displays operatively coupled to the computer;
   a sensor operatively coupled to the computer, the sensor configured to measure at least one biological indicator of stress in the trainee;

software running on the computer, the software presents the training segments to the trainee, simulating operation of the vehicle under control of the trainee through operator controls;

while the software presents the training segments to the trainee, the software reads data from the sensor and the software calculates an instantaneous stress level of the trainee from the data;

when the instantaneous stress level exceeds a first predetermined threshold, the software notifies a trainer; and when the instantaneous stress level does not exceed the first predetermined threshold and the instantaneous stress level exceeds a second predetermined threshold, then the software slows the presentation of the training segments or stops the presentation of the training segments to reduce a complexity of tasks that need be performed by the trainee.

2. The training system of claim 1, wherein if the instantaneous stress level is lower than a third predetermined threshold, then the software speeds the presentation of the training segments to increase the complexity of the tasks that need be performed by the trainee.

3. The training system of claim 1, wherein the sensor recognizes facial expressions of the trainee and the software that calculates the instantaneous stress level of the trainee calculates the instantaneous stress level based upon the facial expressions of the trainee.

4. The training system of claim 1, wherein the sensor measures galvanic skin response of the trainee and the software that calculates the instantaneous stress level of the trainee calculates the instantaneous stress level based upon the galvanic skin response of the trainee.

5. The training system of claim 1, further comprising when the instantaneous stress level does not exceed the first predetermined threshold and the instantaneous stress level exceeds the second predetermined threshold, then the software modifies the training segment by removing pedestrians, changing a grade of a road, widening the road, increasing lighting/visibility, quieting a simulated noise, reducing traffic, removing/adding other vehicles that are driving poorly, changing weather conditions, providing a rest station/pull-off, keeping traffic lights green, and lowering a brightness of a dashboard display, or reducing X/Y/Z movement of the training system.

6. The training system of claim 1, further comprising when the instantaneous stress level does not exceed the first predetermined threshold and the instantaneous stress level exceeds the second predetermined threshold, then the software modifies the training segment by changing a challenge of a road of the training segment, changing a closeness of a trailing vehicle, and changing a clarity of images displayed in side window displays of the training system.

7. A method of training a trainee in a use of a vehicle, the method using a training system having a computer that includes a storage device, the storage device having stored within a plurality of training segments; the training system including a sensor, the sensor configured to measure at least one biological indicator of stress in the trainee, the training system including a seat where the trainee sits during a simulation; the method includes:

(a) presenting one of the training segments in the simulation;

(b) monitoring inputs from the trainee, the inputs controlling an operation of the training system, the inputs from at least a steering device and a throttle device, the steering device and the throttle device are operatively coupled to the computer and are located within the training system;

(c) reading data from the sensor;

(d) calculating an instantaneous stress level of the trainee from the data;

(e) when the instantaneous stress level is greater than a first predetermined value, notifying a trainer;

(f) when the instantaneous stress level is not greater than the first predetermined value and is greater than a second predetermined value, slowing the presentation of the training segments or stopping the presentation of the training segments, thereby reducing complexity of the training segment for reducing the instantaneous stress level of the trainee; and (f) repeating steps a-f.

8. The method of claim 7, further comprising the step of: when the instantaneous stress level is less than a third predetermined value, speeding the presentation of the training segments to increase the complexity of the training and for increasing the instantaneous stress level of the trainee.

9. The method of claim 7, wherein the sensor measures a heart rate of the trainee and the step of calculating the instantaneous stress level of the trainee comprises calculating the instantaneous stress level based upon the heart rate of the trainee.

10. The method of claim 9, wherein the sensor measures galvanic skin response of the trainee and the step of calculating the instantaneous stress level of the trainee includes galvanic skin response the instantaneous stress level based upon the galvanic skin response of the trainee.

11. The method of claim 9, further comprising the step of: if the instantaneous stress level is greater than a fourth predetermined threshold, notifying a first responder if the data indicates a health concern with the trainee.

12. The method of claim 9, further comprising when the instantaneous stress level is not greater than the first predetermined value and is greater than the second predetermined value, modifying the training segment by changing a challenge of a road of the simulation, changing a closeness of a trailing vehicle, and changing a clarity of images displayed in side window displays of the training system.

13. The method of claim 9, further comprising when the instantaneous stress level is not greater than the first predetermined value and is greater than the second predetermined value, modifying the training segment by removing pedestrians from the training segment, changing a grade of a road in the training segment, widening the road in the training segment, increasing lighting/visibility, quieting a simulated noise in the training segment, reducing traffic in the training segment, removing/adding other vehicles that are driving poorly in the training segment, changing weather conditions in the training segment, providing a rest station/pull-off in the training segment, keeping traffic lights green in the training segment, lowering a brightness of a dashboard display in the training segment, or reducing X/Y/Z movement of the training system.

14. A system for training a trainee regarding use of a vehicle the training system having a seat in which the trainee sits, the system comprising:

a computer;

a plurality of training segments accessible by the computer;

a plurality of controls for operation by the trainee, the controls comprising at least a steering device, and a throttle device, the controls operatively coupled to the computer;

a display operatively interfaced to the computer, the display for displaying one or more of the training segments sequentially to simulate an operation of the vehicle, the one or more training segments responsive to operation of the controls by the trainee;

at least one sensor is operatively coupled to the computer, the at least one sensor configured to measure at least one biological indicator of instantaneous stress in the trainee;

software running on the computer causes the computer to present the training segments and to calculate an instantaneous stress level of the trainee from the at least one biological indicator;

when the instantaneous stress is greater than a first predetermined threshold, the software running on the computer causes the computer to notifying a trainer; and when the instantaneous stress level is less than or equal to the first predetermined threshold and greater than a second predetermined threshold, the software running on the computer slows the presentation of the training segments or stops the presentation of the training segments to reduce to reduce a complexity of the training segment, thereby a complexity of the training segment is reduced for reducing the instantaneous stress of the trainee.

15. The system for training the trainee regarding the use of the vehicle of claim 14, wherein when the instantaneous stress level is lower than a third predetermined threshold, the software running on the computer slows the presentation of the training segments to increase the complexity of the training segment, thereby the complexity of the training segment is increased for increasing the instantaneous stress of the trainee.

16. The system for training the trainee regarding the use of the vehicle of claim 14, wherein when the instantaneous stress level is less than or equal to the first predetermined threshold and greater than a second predetermined threshold, the software running on the computer increases a challenge of a road of the training segment, reduces a closeness of a trailing vehicle of the training segment, or changes a clarity of images displayed in side window displays of the training system.

17. The system for training the trainee regarding the use of the vehicle of claim 14, wherein when the instantaneous stress level is less than or equal to the first predetermined threshold and greater than a second predetermined threshold, the software running on the computer removing pedestrians of the training segment, changes a grade of a road of the training segment, widens a road of the training segment, increases lighting/visibility of the training segment, quiets a simulated noise of the training segment, reduces traffic of the training segment, removing/adding other vehicles that are driving poorly in the training segment, changing weather conditions of the training segment, providing a rest station/pull-off in the training segment, keeps traffic lights green in the training segment, lowers a brightness of a dashboard display of the training segment, or reduces X/Y/Z movement of the training system.

18. The system for training the trainee regarding the use of the vehicle of claim 16, wherein the sensor measures a heart rate of the trainee and the software running on the computer causes the computer to calculate the instantaneous stress of the trainee from based upon the heart rate of the trainee.

19. The system for training the trainee regarding the use of the vehicle of claim 16, wherein the sensor measures galvanic skin response of the trainee and the software causes the computer to calculate the instantaneous stress level based upon the galvanic skin response of the trainee.

20. The system for training the trainee regarding the use of the vehicle of claim 16, wherein the sensor recognizes facial expressions of the trainee and the software running on the computer causes the computer to calculate the instantaneous stress level of the trainee based upon the facial expressions of the trainee.

* * * * *